(12) United States Patent
Adamo et al.

(10) Patent No.: US 11,819,222 B2
(45) Date of Patent: Nov. 21, 2023

(54) DEPTH STOP INSTRUMENT FOR USE IN SPINAL SURGERY

(71) Applicant: SPINE WAVE, INC., Shelton, CT (US)

(72) Inventors: Benoit Adamo, South Salem, NY (US); David Boisvert, Southington, CT (US); Scott McLean, Sandy Hook, CT (US)

(73) Assignee: SPINE WAVE, INC., Shelton, CT (US)

( * ) Notice: Subject to any disclaimer, the term of this patent is extended or adjusted under 35 U.S.C. 154(b) by 251 days.

(21) Appl. No.: 17/118,849

(22) Filed: Dec. 11, 2020

(65) Prior Publication Data

US 2021/0093467 A1 Apr. 1, 2021

Related U.S. Application Data

(62) Division of application No. 16/150,335, filed on Oct. 3, 2018, now Pat. No. 10,888,434.

(Continued)

(51) Int. Cl.
*A61B 17/16* (2006.01)
*A61F 2/46* (2006.01)
(Continued)

(52) U.S. Cl.
CPC ...... *A61B 17/1626* (2013.01); *A61B 17/1633* (2013.01); *A61F 2/447* (2013.01);
(Continued)

(58) Field of Classification Search
CPC .................. A61B 17/1626; A61B 17/1633
See application file for complete search history.

(56) References Cited

U.S. PATENT DOCUMENTS

| 2,998,007 A | 8/1961 | Herzog |
| 3,574,381 A | 4/1971 | Ocheltree et al. |

(Continued)

FOREIGN PATENT DOCUMENTS

| EP | 0 064 724 A2 | 11/1982 |
| FR | 2827156 A1 | 1/2003 |

OTHER PUBLICATIONS

International Search Report for PCT/US2018/054092, dated Dec. 31, 2018.

(Continued)

*Primary Examiner* — Amy R Sipp
(74) *Attorney, Agent, or Firm* — Hoffmann and Baron, LLP

(57) ABSTRACT

A disc preparation instrument for use in fusing spinal vertebrae comprises a modular scoring trial and a depth stop releasably attached to the scoring trial. The trial includes an elongate stem supporting a trial device at its distal tip. The trial device is insertable into a disc space and includes a rotatable rasp for scoring opposing vertebral endplates at a scored location. A stop, sized to engage an exterior surface of the vertebrae, is movable on the depth stop stem by rotation of an adjustment knob to a plurality of selectable distances between the proximal end of the trial device and the movable stop. An actuator releasably attached to the trial is operable to rotate the rasp. A plurality of modular trials, each having a trial device of different heights may be provided in a kit. Each scoring trial is selectively releasably attachable to a single depth stop.

8 Claims, 13 Drawing Sheets

Related U.S. Application Data

(60) Provisional application No. 62/570,179, filed on Oct. 10, 2017, provisional application No. 62/568,575, filed on Oct. 5, 2017.

(51) Int. Cl.
*A61F 2/44* (2006.01)
*A61F 2/30* (2006.01)

(52) U.S. Cl.
CPC .......... *A61F 2/4603* (2013.01); *A61F 2/4611* (2013.01); *A61F 2/4684* (2013.01); *A61F 2/4455* (2013.01); *A61F 2002/30507* (2013.01); *A61F 2002/30537* (2013.01); *A61F 2002/30616* (2013.01); *A61F 2002/4625* (2013.01); *A61F 2220/0025* (2013.01); *A61F 2230/0069* (2013.01)

(56) References Cited

U.S. PATENT DOCUMENTS

| | | | |
|---|---|---|---|
| 3,814,089 A | 6/1974 | Deyerle | |
| 4,275,717 A | 6/1981 | Bolesky | |
| 4,519,100 A | 5/1985 | Wills et al. | |
| 4,667,664 A | 5/1987 | Taylor et al. | |
| 4,848,327 A | 7/1989 | Perdue | |
| 4,892,545 A | 1/1990 | Day et al. | |
| 5,057,103 A | 10/1991 | Davis | |
| 5,397,364 A | 3/1995 | Kozak et al. | |
| 5,522,899 A | 6/1996 | Michelson | |
| 5,534,004 A | 7/1996 | Santangelo | |
| 5,601,550 A | 2/1997 | Esser | |
| 5,782,830 A | 7/1998 | Farris | |
| 5,800,550 A | 9/1998 | Sertich | |
| 5,810,820 A | 9/1998 | Santori et al. | |
| 5,895,389 A * | 4/1999 | Schenk ................. | A61B 17/17 606/80 |
| 5,971,986 A | 10/1999 | Santori et al. | |
| 5,976,139 A | 11/1999 | Bramlet | |
| 6,030,401 A | 2/2000 | Marino | |
| 6,077,264 A | 6/2000 | Chemello | |
| 6,083,225 A | 7/2000 | Winslow et al. | |
| 6,099,531 A | 8/2000 | Bonutti | |
| 6,120,503 A | 9/2000 | Michelson | |
| 6,174,311 B1 | 1/2001 | Branch et al. | |
| 6,179,873 B1 | 1/2001 | Zientek | |
| 6,183,474 B1 | 2/2001 | Bramlet et al. | |
| 6,235,059 B1 | 5/2001 | Benezech et al. | |
| 6,342,057 B1 | 1/2002 | Brace et al. | |
| 6,342,074 B1 | 1/2002 | Simpson | |
| 6,379,364 B1 | 4/2002 | Brace et al. | |
| 6,409,768 B1 | 6/2002 | Tepic et al. | |
| 6,443,954 B1 | 9/2002 | Bramlet et al. | |
| 6,447,546 B1 | 9/2002 | Bramlet et al. | |
| 6,468,311 B2 | 10/2002 | Boyd et al. | |
| 6,527,803 B1 | 3/2003 | Crozet et al. | |
| 6,558,388 B1 | 5/2003 | Bartsch et al. | |
| 6,558,423 B1 | 5/2003 | Michelson | |
| 6,648,889 B2 | 11/2003 | Bramlet et al. | |
| 6,770,096 B2 | 8/2004 | Bolger et al. | |
| 7,056,344 B2 | 6/2006 | Huppert et al. | |
| 7,223,289 B2 | 5/2007 | Trieu et al. | |
| 7,232,464 B2 | 6/2007 | Mathieu et al. | |
| 7,235,082 B2 | 6/2007 | Bartish et al. | |
| 7,416,553 B2 | 8/2008 | Patel et al. | |
| 7,594,931 B2 | 9/2009 | Louis et al. | |
| 7,674,287 B2 | 3/2010 | Alferness et al. | |
| 7,695,516 B2 | 4/2010 | Zeegers | |
| 7,749,271 B2 | 7/2010 | Fischer et al. | |
| 7,776,047 B2 | 8/2010 | Fanger et al. | |
| 7,842,088 B2 | 11/2010 | Rashbaum et al. | |
| 7,846,207 B2 | 12/2010 | Lechmann et al. | |
| 7,909,829 B2 | 3/2011 | Patel et al. | |
| 7,909,848 B2 | 3/2011 | Patel et al. | |
| 7,935,123 B2 | 5/2011 | Fanger et al. | |
| 7,988,693 B2 | 8/2011 | Martz et al. | |
| 8,002,776 B2 | 8/2011 | Liu et al. | |
| 8,062,303 B2 | 11/2011 | Berry et al. | |
| 8,080,062 B2 | 12/2011 | Armstrong et al. | |
| 8,147,556 B2 | 4/2012 | Louis et al. | |
| 8,216,313 B2 | 7/2012 | Moore | |
| 8,257,439 B2 | 9/2012 | Zeegers | |
| 8,267,997 B2 | 9/2012 | Colleran | |
| 8,268,000 B2 | 9/2012 | Waugh et al. | |
| 8,273,127 B2 | 9/2012 | Jones et al. | |
| 8,282,682 B2 | 10/2012 | Kirschman | |
| 8,292,958 B1 | 10/2012 | Bruffey et al. | |
| 8,313,528 B1 | 11/2012 | Wensel | |
| 8,328,870 B2 | 12/2012 | Patel et al. | |
| 8,328,872 B2 | 12/2012 | Duffield et al. | |
| 8,337,500 B2 | 12/2012 | Bertagnoli et al. | |
| 8,343,219 B2 | 1/2013 | Allain et al. | |
| 8,377,133 B2 | 2/2013 | Yuan et al. | |
| 8,394,107 B2 | 3/2013 | Fanger et al. | |
| 8,409,285 B2 | 4/2013 | Keller | |
| 8,454,700 B2 | 6/2013 | Lemoine et al. | |
| 8,460,388 B2 | 6/2013 | Kirwan et al. | |
| 8,523,946 B1 | 9/2013 | Swann | |
| 8,617,245 B2 | 12/2013 | Brett | |
| 8,641,766 B2 | 2/2014 | Donner et al. | |
| 8,685,104 B2 | 4/2014 | Lee et al. | |
| 8,709,083 B2 | 4/2014 | Duffield et al. | |
| 8,728,165 B2 | 5/2014 | Parry et al. | |
| 8,840,651 B2 | 9/2014 | Reiley | |
| 8,864,830 B2 | 10/2014 | Malandain | |
| 8,906,101 B2 | 12/2014 | Lee et al. | |
| 8,932,359 B2 | 1/2015 | Brett | |
| 8,968,405 B2 | 3/2015 | Kirwan et al. | |
| 9,033,993 B2 | 5/2015 | Bae et al. | |
| 9,039,774 B2 | 5/2015 | Chataigner et al. | |
| 9,044,337 B2 | 6/2015 | Dinville et al. | |
| 9,078,765 B2 | 7/2015 | Louis et al. | |
| 9,101,489 B2 | 8/2015 | Protopsaltis et al. | |
| 9,155,631 B2 | 10/2015 | Seifert et al. | |
| 9,161,841 B2 | 10/2015 | Kana et al. | |
| 9,216,024 B2 | 12/2015 | Geisert et al. | |
| 9,241,809 B2 | 1/2016 | McDonough et al. | |
| 9,358,134 B2 | 6/2016 | Malandain | |
| 9,381,098 B2 | 7/2016 | Gittings et al. | |
| 9,402,740 B1 | 8/2016 | Donaldson | |
| 9,402,741 B1 | 8/2016 | Donaldson | |
| 9,572,685 B2 | 2/2017 | Perry | |
| 9,937,055 B1 | 4/2018 | Bernhardt, Jr. et al. | |
| 2001/0011191 A1 | 8/2001 | Kohrs | |
| 2004/0082955 A1 | 4/2004 | Zirkle, Jr. | |
| 2005/0027300 A1 | 2/2005 | Hawkins et al. | |
| 2007/0123985 A1 | 5/2007 | Errico | |
| 2007/0239168 A1 | 10/2007 | Kuenzi et al. | |
| 2007/0250167 A1 | 10/2007 | Bray et al. | |
| 2008/0027550 A1 | 1/2008 | Link | |
| 2008/0243131 A1 | 10/2008 | Sorrenti et al. | |
| 2008/0249569 A1 | 10/2008 | Waugh et al. | |
| 2008/0281425 A1 | 11/2008 | Thalgott et al. | |
| 2009/0099601 A1 | 4/2009 | Aferzon et al. | |
| 2009/0164020 A1 | 6/2009 | Janowski et al. | |
| 2010/0016968 A1 | 1/2010 | Moore | |
| 2010/0145459 A1 | 6/2010 | McDonough et al. | |
| 2010/0185289 A1 | 7/2010 | Kirwan et al. | |
| 2011/0098747 A1 | 4/2011 | Donner et al. | |
| 2011/0208311 A1 | 8/2011 | Janowski | |
| 2012/0078373 A1 | 3/2012 | Gamache et al. | |
| 2012/0116466 A1 | 5/2012 | Dinville et al. | |
| 2012/0191166 A1 | 7/2012 | Louis et al. | |
| 2012/0197263 A1 | 8/2012 | Copf et al. | |
| 2012/0197401 A1 | 8/2012 | Duncan et al. | |
| 2012/0253406 A1 | 10/2012 | Bae et al. | |
| 2012/0277872 A1 | 11/2012 | Kana et al. | |
| 2012/0277873 A1 | 11/2012 | Kana et al. | |
| 2013/0110242 A1 | 5/2013 | Kirwan et al. | |
| 2013/0150968 A1 | 6/2013 | Dinville et al. | |
| 2013/0226300 A1 | 8/2013 | Chataigner et al. | |
| 2013/0245767 A1 | 9/2013 | Lee et al. | |
| 2014/0088711 A1 | 3/2014 | Chin et al. | |
| 2014/0114413 A1 | 4/2014 | Allain et al. | |

(56) References Cited

U.S. PATENT DOCUMENTS

| | | |
|---|---|---|
| 2014/0142619 A1 | 5/2014 | Serina et al. |
| 2014/0156010 A1 | 6/2014 | Lee et al. |
| 2014/0163684 A1 | 6/2014 | Donner et al. |
| 2014/0277456 A1 | 9/2014 | Kirschman |
| 2014/0277477 A1 | 9/2014 | Malandain |
| 2015/0051702 A1 | 2/2015 | Chataigner et al. |
| 2015/0051704 A1 | 2/2015 | Duffield et al. |
| 2015/0057754 A1 | 2/2015 | Reed et al. |
| 2015/0127107 A1 | 5/2015 | Kim et al. |
| 2015/0127109 A1 | 5/2015 | Brett |
| 2015/0202051 A1 | 7/2015 | Tanaka et al. |
| 2015/0209089 A1 | 7/2015 | Chataigner et al. |
| 2015/0305883 A1 | 10/2015 | Garber et al. |
| 2015/0305887 A1 | 10/2015 | McAtamney et al. |
| 2016/0015523 A1 | 1/2016 | Lewis et al. |
| 2016/0151168 A1 | 6/2016 | Morris et al. |
| 2017/0112631 A1 | 4/2017 | Kuyler |

OTHER PUBLICATIONS

Written Opinion for PCT/US2018/054092, dated Dec. 31, 2018.
International Search Report for PCT/US18/54088, dated Feb. 11, 2019.
Written Opinion for PCT/US18/54088, dated Feb. 11, 2019.

* cited by examiner

DEPTH STOP INSTRUMENT FOR USE IN SPINAL SURGERY

CROSS-REFERENCE TO RELATED APPLICATION

This application is a divisional application of U.S. application Ser. No. 16/150,335, filed Oct. 3, 2018, now pending, which claims the benefit of U.S. Provisional Patent Application No. 62/568,575, filed Oct. 5, 2017, and U.S. Provisional Patent Application No. 62/570,179, filed Oct. 10, 2017, the entire contents of such applications being incorporated by reference herein.

FIELD OF THE INVENTION

The subject invention relates generally to the field of spinal instrumentation and more particularly to a spinal disc preparation instrument for use in fusing together a superior vertebra and an inferior vertebra, the disc preparation instrument including a modular scoring trial and a releasable depth stop.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

One embodiment of a spinal device for cervical fusion is described in U.S. Patent Publication No. 2015/0202051, entitled "Spinal Fusion System", filed on Jan. 16, 2015 by Shigeru Tanaka et al. (the '051 Application) and assigned to the same assignee as the subject application. The entire contents of the '051 Application are incorporated herein by reference. The spinal fusion system described in the '051 Application includes an interbody fusion cage, a fixation plate with deployable anchor blades, and an implanter. In a particular arrangement described in the '051 Application, the system may further include a trial/sizer tool including a set of trial/sizer instruments. Such instruments may incorporate a pre-scoring blade to break the vertebral endplate prior to insertion of the spinal implant into the disc space and deployment of the blades into the endplates. As such, the trial device may serve two purposes, namely to test a size for a potential interbody fusion cage implant and to prepare one or more vertebral endplate surfaces for receiving the implant.

Another example of a scoring trial particularly useful in cervical fusion is shown and described in U.S. patent application Ser. No. 15/454,287, entitled "Scoring Implant Trial and Implant Inserter for Spinal Fusion System", filed on Mar. 9, 2017 by Andrew Bernhardt, Jr. et al. (the '287 Application) and assigned to the same assignee as the subject application. The entire contents of the '287 Application are incorporated herein by reference. The scoring trial described in the '287 application in one arrangement includes a trial device on one end that approximates the size and shape of the cage implant, a depth stop element to limit over-insertion into the disc space, and a rotating rasp element to slot the surfaces of the vertebral endplates on the superior and inferior faces at a controlled distance from the depth stop. The scoring element is positioned within the trial device at a location suitable for creating slots in the vertebral endplates that correspond to entry locations for blades on an anchor plate to penetrate the vertebral endplates. The scoring element is actuated rotationally about the long axis of the instrument by a turning a T-handle at the opposite end of the device in an oscillating fashion.

While the scoring function of the devices of the '051 Application and '287 Application is beneficial in spinal surgical procedures, certain features in such scoring trials tend to add additional bulk to the instrument making the devices more cumbersome during use. In some cases, surgeons may opt to use standard trials without scoring capability for the sizing function, as several passes of various sized trials may be required to determine the appropriate implant size, and to employ the scoring trial only after the size has been determined. Offering both forms of trials is costly and undesirable due to the additional space required in sterilization trays.

SUMMARY OF THE INVENTION

It is an object of the subject invention is to provide a compact trial offering that includes the desirable features of both the standard trials and scoring trials. A further object is to provide a kit comprising a plurality of modular scoring trials and a depth stop that is selectively releasably attachable to each of the modular scoring trials for a more compact, lower cost instrument offering.

DESCRIPTION OF THE EMBODIMENTS

Figure 1:
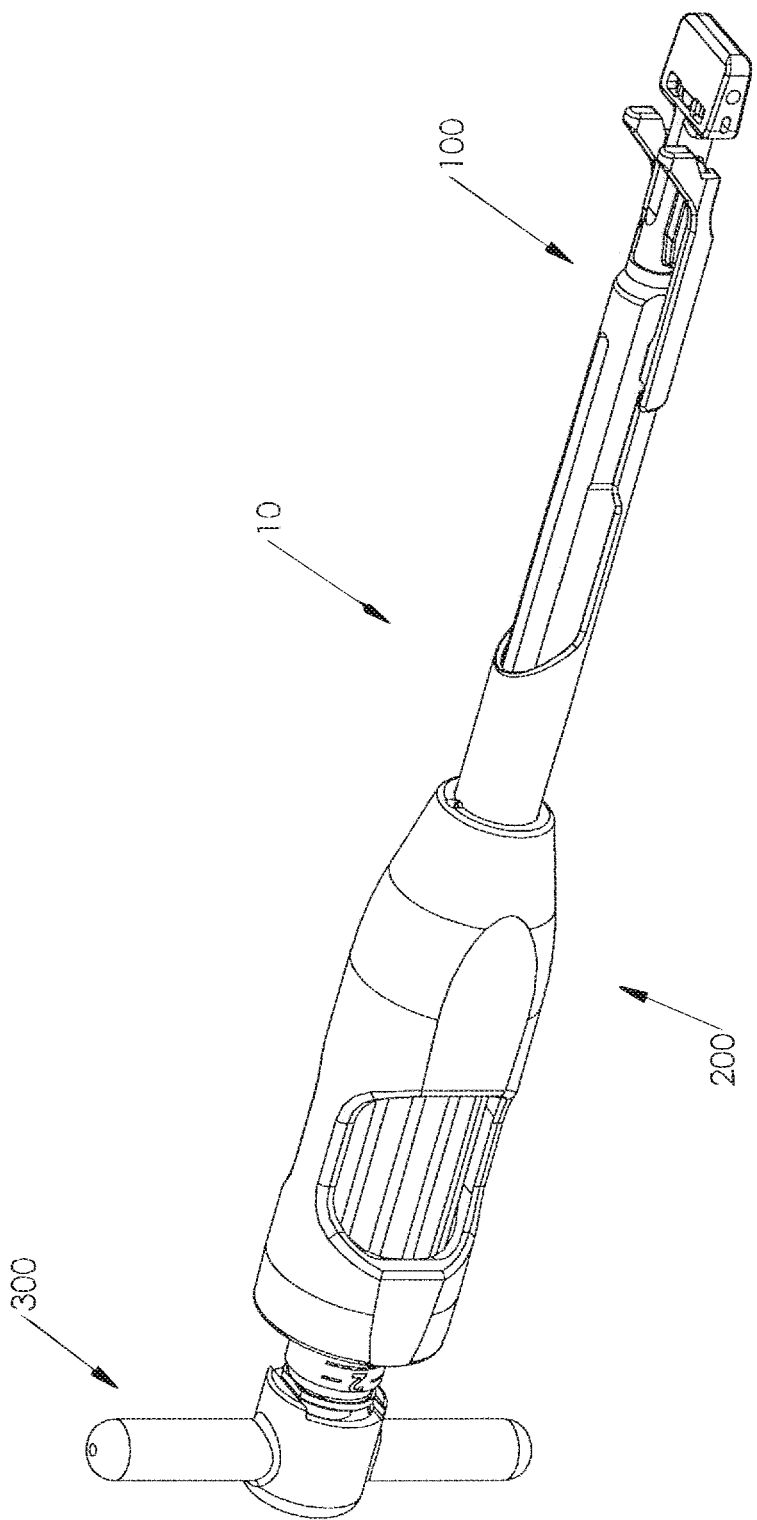
FIG. 1 is a top perspective view of a disc preparation instrument, in accordance with one embodiment of the present invention, for use in fusing together opposing vertebra of a spine.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
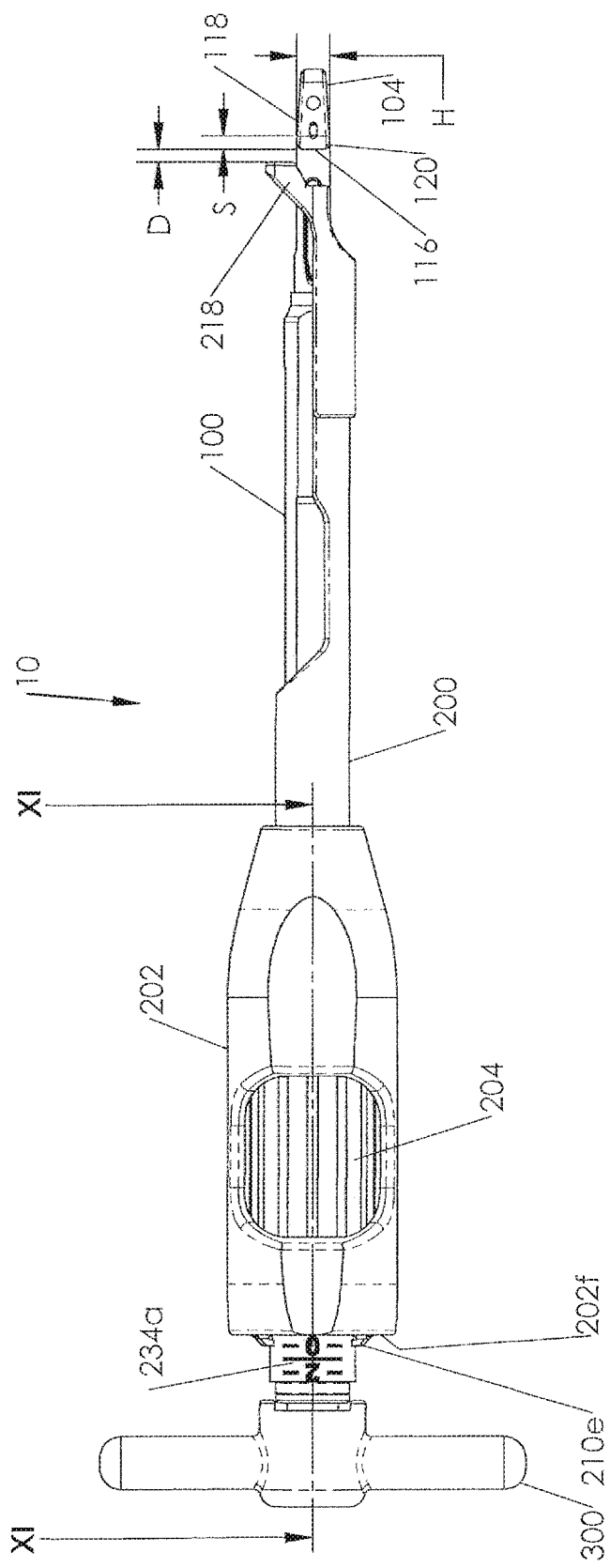
FIG. 2 is a side elevation view of the disc preparation instrument of FIG. 1.
Figure 3:
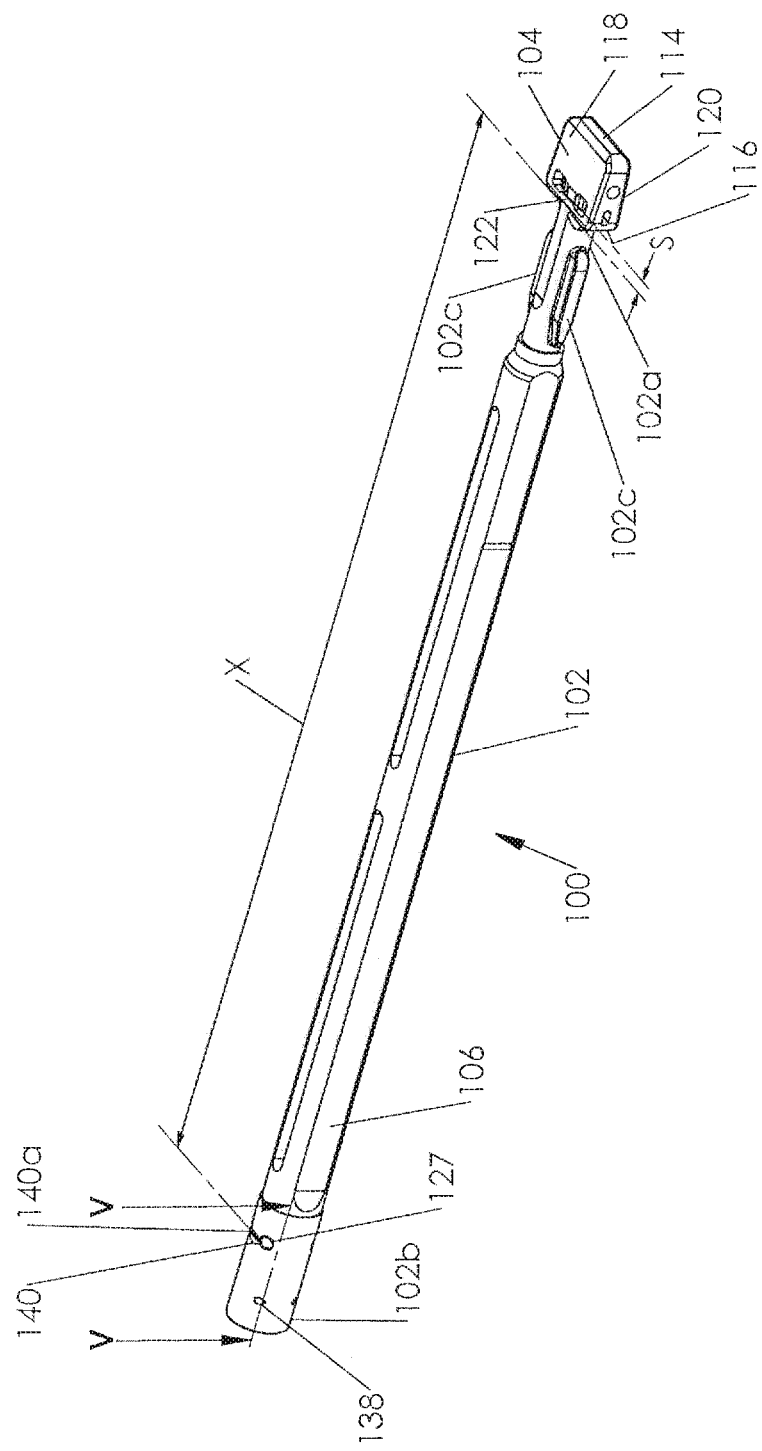
FIG. 3 is a top perspective view of the modular scoring trial of the disc preparation instrument of FIG.

The present invention contemplates a disc preparation instrument as depicted in FIGS. 1-3 for use in fusing together opposing superior and inferior vertebra of a spine. Instrument 10 comprises a modular scoring trial 100, a depth stop 200 that is releasably attached to scoring trial 100, and an actuator 300 shown in a particular form as a T-handle. Disc preparation instrument 10 provides a scoring element, as will be described, that scribes vertebral endplates at an appropriate anterior-posterior location for anchor blades on an anterior cervical cage to engage the vertebral bodies. An inserter which replicates the anterior-posterior distance scribed by the disc preparation instrument is used to insert the cervical cage into the disc space to the measured depth so that the blades will be deployed into the slots created by the scoring element. Such an inserter and anterior cervical cage are described in the '287 Application, commonly assigned herewith. Alternatively, the inserter described in U.S. application Ser. No. 16/150,344, entitled "Modular Inserter for Anterior Cervical Cage", filed on Oct. 3, 2018, by Benoit Adamo, et al. (the '344 Application), may also be used in conjunction with the subject disc preparation tool to insert an anterior cervical cage for interbody fusion. The '344 Application is assigned to the same assignee as the subject invention and is incorporated by reference herein in its entirety. It should be appreciated, however, that disc preparation instrument 10 may also be used in interbody fusion procedures in other regions of the spine.

Turning now also to FIGS. 3, 4, 5 and 6A-D, the details of modular scoring trial 100 are described. Scoring trial 100 comprises an elongate stem 102 having a distal end 102a and a proximal end 102a and a trial device 104 fixedly supported on the distal end 102a of the stem 102. Elongate stem 102 is of generally cylindrical configuration having a pair of diametrically opposing substantially parallel flat surfaces 106 extending substantially along the length of stem 102 between distal end 102a and proximal end 102b. A lumen 108 (see FIG. 10) extends substantially centrally throughout the length of stem 102, lumen 108 opening through both the distal end 102a and the proximal end 102b. A counterbore 110 communicating with lumen 108 is formed at the proximal end 102b of stem 102, counterbore 110 including an interior surface 110a having a diameter greater than the diameter of lumen 108. Counterbore 110 terminates interiorly of stem 102 in a transverse surface 112 extending transversely between counterbore 110 and lumen 108. Adjacent distal end 102a and disposed distally of flat surfaces 106, elongate stem 102 includes a pair of diametrically opposed stabilizers 102c projecting outwardly radially therefrom, the purpose of which will be described hereinbelow.

Trial device 104 has a distal end 114, a proximal end 116, a top surface 118 and a bottom surface 120. Top surface 118 has a top opening 118a and bottom surface 120 has a bottom opening (not shown) similar to top opening 118a. Trial device 104 supports a rotatably movable scoring element 122 disposed between distal end 114 and proximal end 116 and having a first portion 122a and a second portion 122b. The proximal surface of scoring element 122 is disposed at a predetermined spacing, S from proximal end 116 of trial device 104, as shown in FIG. 3. Scoring element 122 is selectively movable from a first position wherein first portion 122a and second portion 122b are both disposed interiorly of trial device 104 as shown in FIG. 3 to a second position (shown in FIG. 12) wherein first portion 122a extends exteriorly of trial device 104 through top opening 118a and second portion 122b extends exteriorly of trial device 104 through the bottom opening. First portion 122a and second portion 122 each includes in a particular aspect a rasped scoring surface along the edges thereof to facilitate scoring of the surfaces of vertebral endplates, although other abrasive surfaces may also be used. Trial device 104 may be used for the dual purpose of scoring and trialing but could be used only for scoring. In the dual configuration, trial device 104 is of size and configuration approximating the size and configuration of a fusion cage intended for insertion into the disc space. In this regard, trial device 104 has a maximum height, H between top surface 118 and bottom surface 120, as illustrated in FIG. 2. Trial device 104 may also be formed to taper downwardly toward distal end 114 defining trial device 104 to have a lordotic configuration, as also seen in FIG. 2.

Figure 4:
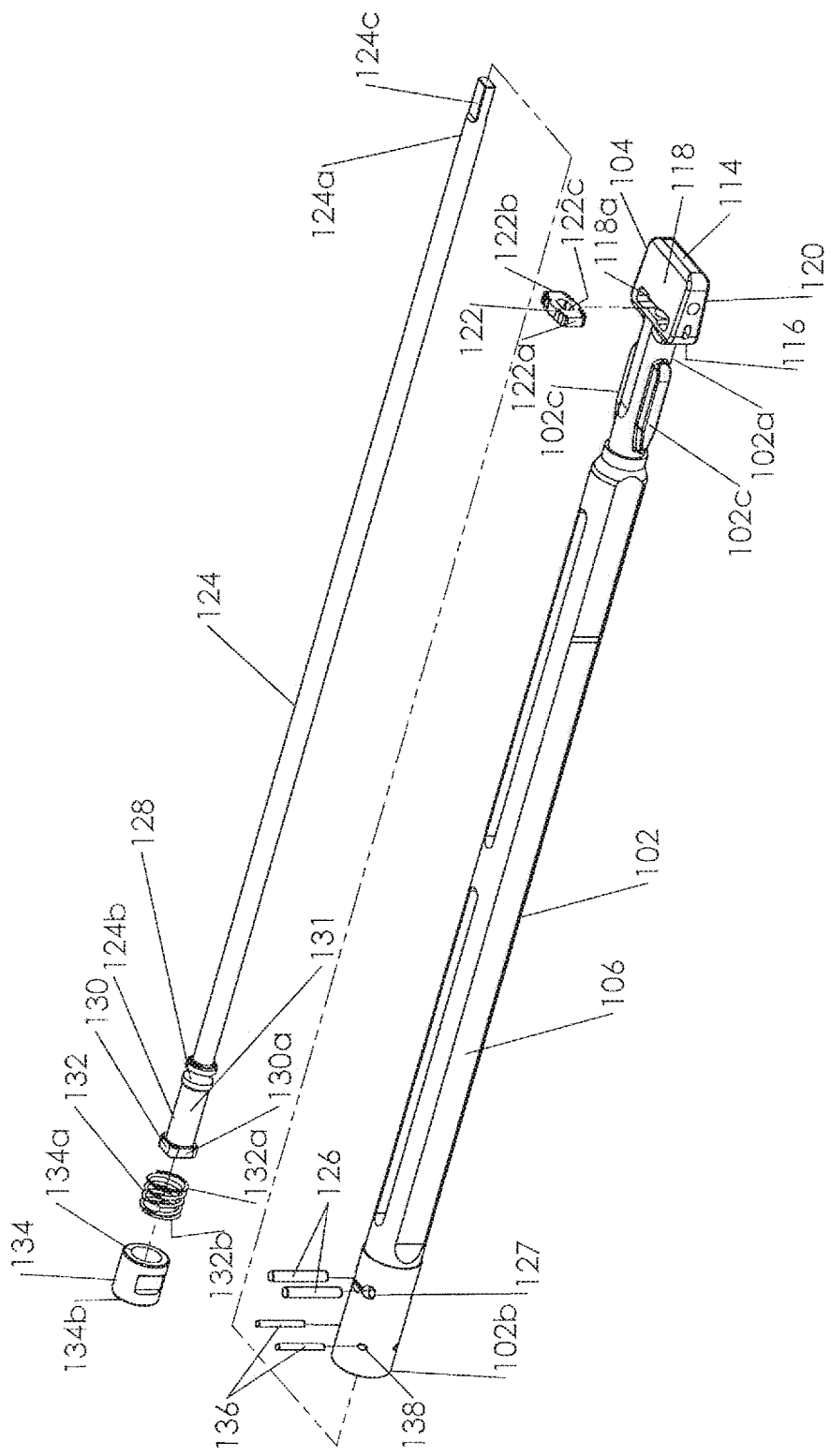
FIG. 4 is a top perspective exploded view of the modular scoring trial shown in FIG. 3.

As illustrated in FIG. 4, an elongate shaft 124 having a distal end 124a and a proximal end 124b extends within lumen 108 of stem 102. Elongate shaft 124 is rotatable but not axially translatable within lumen 108. Axial translation of shaft 124 relative to stem 102 is prevented by a pair of pins 126 extending through a pair of openings 127 extending through proximal end 102b of stem 102 and disposed in a groove 128 extending around the circumference of shaft 124. Distal end 124a includes an engagement feature 124c for extending into trial device 104 and engaging scoring element 122. In one particular arrangement, engagement feature 124c is a multi-faceted drive with opposing flat surfaces, sized and configured to engage with a complementary sized and configured opening 122c formed in scoring element 122. Shaft 124 has at its proximal end 124b a drive element 130 for engagement with actuator 300 for rotating shaft 124 and scoring element 122, as will be described. Drive element 130 includes a non-circular configuration and, in a particular arrangement, comprises a square drive having four substantially flat mutually orthogonal engagement surfaces 130a. At least one of such flat surfaces 130a is formed to be in alignment with a flat surface of engagement feature 124c in a manner to fully retain scoring element 122 within trial device 104 when scoring element 122 is in the first position as described hereinabove. Shaft 124 is of length such that when engagement feature 124c is in engagement with scoring element 122, drive element 130 is disposed within counterbore 110 at the distal end 102b of stem 102, as depicted in FIG. 5.

Figure 6B:
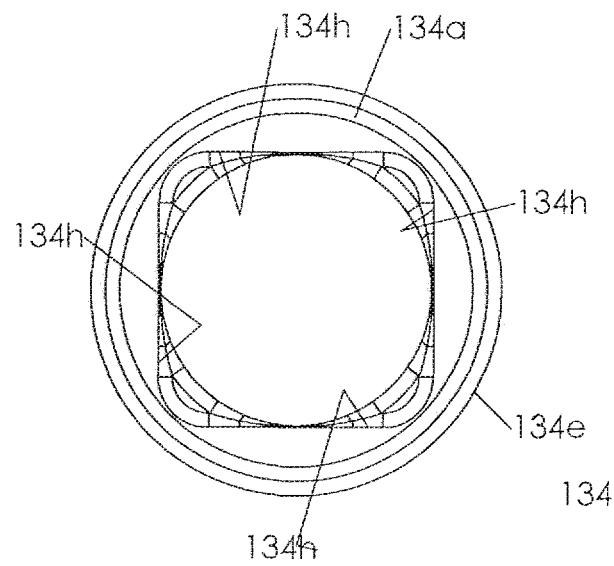
FIG. 6B is an end view of the locking element of FIG. 6A.
Figure 6C:
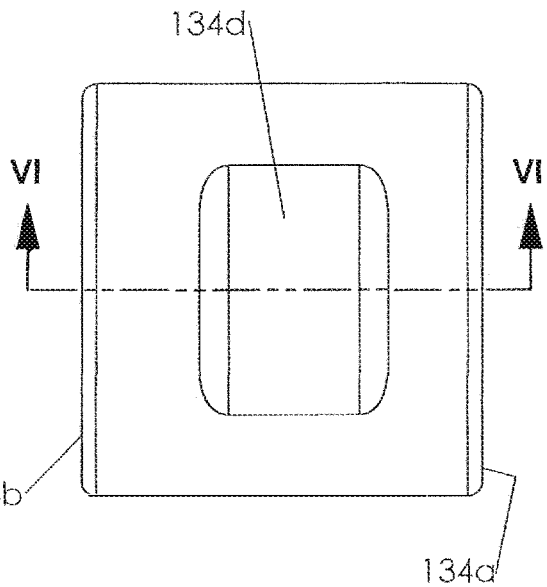
FIG. 6C is a side elevation view of the locking element of FIG. 6A.
Figure 6A:
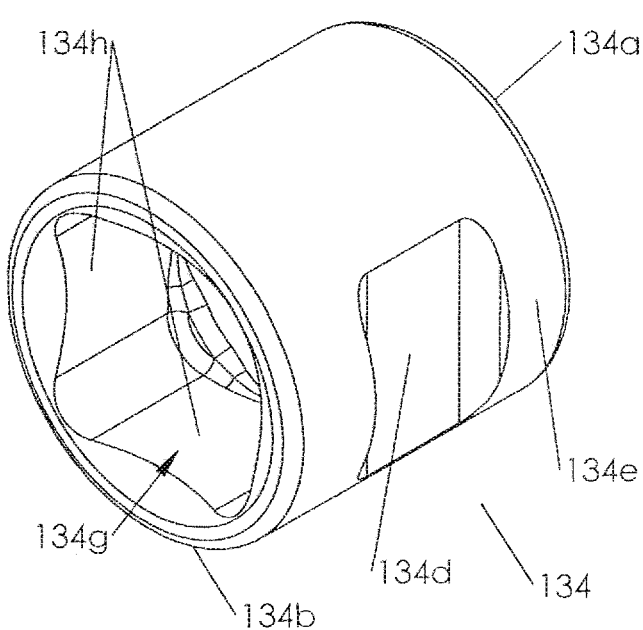
FIG. 6A is a perspective view of the locking element of the modular scoring trial shown in FIG. 3.
Figure 6D:
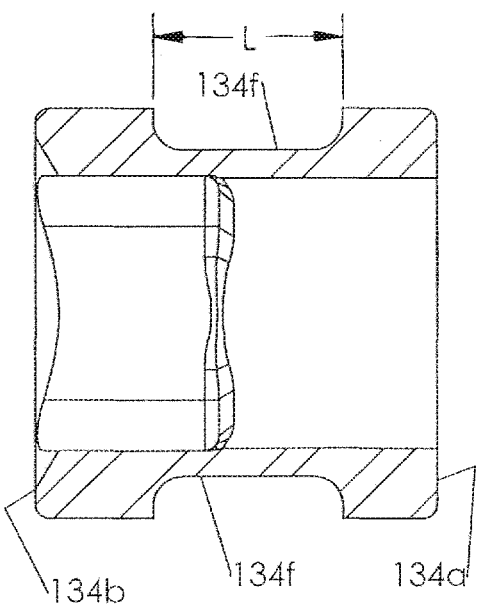
FIG. 6D is a longitudinally sectioned view of the locking element as seen along viewing lines VI-VI of FIG. 6C.

Shaft 124 includes a generally cylindrical locking element support surface 131 between circumferential groove 128 and drive element 130. Disposed on support surface 131 and within counterbore 110 at the distal end 102b stem 102 is a spring element 132 and a locking element 134. In a particular arrangement, spring element 132 is a coil spring of generally cylindrical configuration having a distal end 132a and a proximal end 132b. As shown in more detail in FIGS. 6A-D, locking element 134 is of generally cylindrical configuration having a distal end 134a, a proximal end 134b and an interior surface 134c therebetween. Locking element 134 includes a pair of diametrically opposed substantially parallel exterior flat surfaces 134d formed in an outer wall 134e of locking element 134. As such, flat surfaces 134d define a pair of recesses 134f that extend for a length L between distal end 134a and proximal end 134b, as shown in FIG. 6D. Locking element 134 comprises on its interior surface 134c at its proximal end 134b a locking surface 134g that is complementary with the non-circular configuration of drive element 130 at the proximal end 124b of elongate shaft 124. In a particular configuration, locking surface 134g comprises a square socket including four substantially flat mutually orthogonal interior engagement surfaces 134h, as shown in FIGS. 6A and 6B, each surface 134h being sized and configured to releasably engage a respective flat surface 130a of drive element 130. Exterior flat surfaces 134d are oriented to be substantially parallel with two of said engagement surfaces 134h and with flat surfaces 106 of stem 102 so as to provide proper orientation of shaft 124 relative to stem 102 when locking element 134 is assembled to stem 102.

Figure 5:
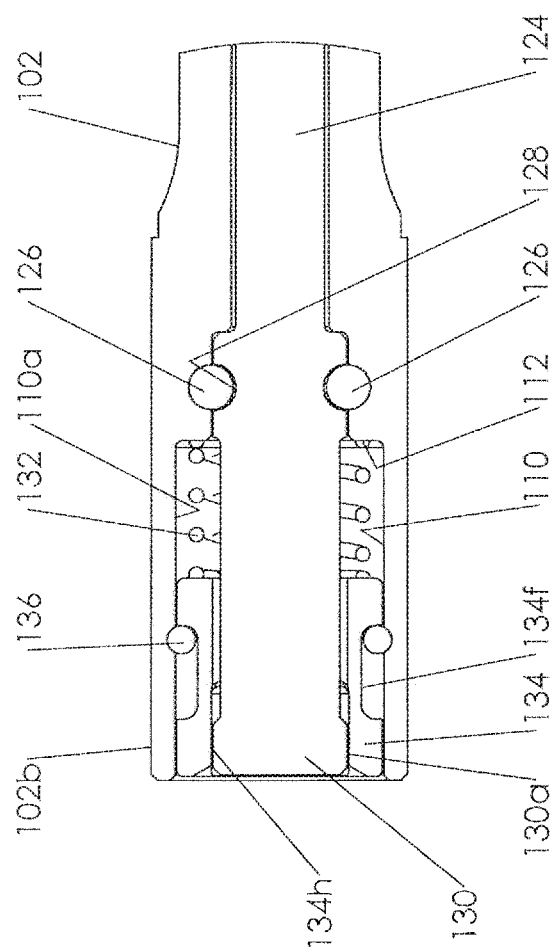
FIG. 5 is a sectional view of a proximal portion of the modular scoring trial as seen along viewing lines V-V of FIG. 3.

Upon assembly with shaft 124, spring element 132 is initially introduced into counterbore 110 at proximal end 102b of stem 102 until spring element distal end 132a contacts interior transverse surface 112, as seen in FIG. 5. Locking element 134 is then introduced into counterbore 110 with distal end 134a engaging spring element proximal end 132b and compressing spring element 132 against transverse interior surface 112, as shown in FIG. 5. A pair of pins 136 is introduced through openings 138 formed through proximal end 102b of stem 102 to movably attach locking element 134 to stem 102, with pins residing in locking element recesses 134f, as shown in FIG. 5. Pins 136 are disposed sufficiently close to locking element exterior flat surfaces 134d to substantially prevent rotational movement of locking element 134 relative to stem 102 within counterbore 110 while allowing relative axial translation. The extent of axial translation of locking element 134 within counterbore 110 is governed by the length L of recesses 134f formed in locking element 134. As depicted in the position shown in FIG. 5, spring 132 is compressed within counterbore 110 thereby providing an axial bias force against locking element 134 toward the proximal end of stem 102 with pins 136 residing in recesses 134f maintaining the bias force. In this first position, flat surfaces 134h of locking element 134 are in releasable engagement with flat surfaces 130a of drive element 130, thereby preventing rotation of shaft 124 relative to stem 102 while the bias force is applied. Upon application of an axial force in the distal direction against locking element 134 sufficient to overcome the bias force of spring element 132 as will be described, locking element 134 is moved in a distal direction to a second position whereby flat locking surfaces 134h of locking element 134 are disengaged from drive element 130 to thereby allow rotation of elongate shaft 124 relative to stem 102.

To releasably attach depth stop 200 to scoring trial 100, an attachment location 140 is provided on elongate stem 102 at the proximal end thereof, as shown in FIG. 3. In a particular arrangement, attachment location 140 comprises a pair of diametrically opposed locking grooves 140a disposed between the respective openings 127 that are provided to receive pins 126. Attachment location 140 is set at a fixed predetermined distance, X from a first location on trial device 104, such as proximal end 116, as illustrated in FIG. 3. It should be appreciated that the first location on trial device 104 may also be defined by scoring element 122. Grooves 140a of attachment location 140 are oriented in one particular arrangement to be on a line that is substantially parallel with the height, H of trial device 104 of scoring trial 100.

Figure 7:
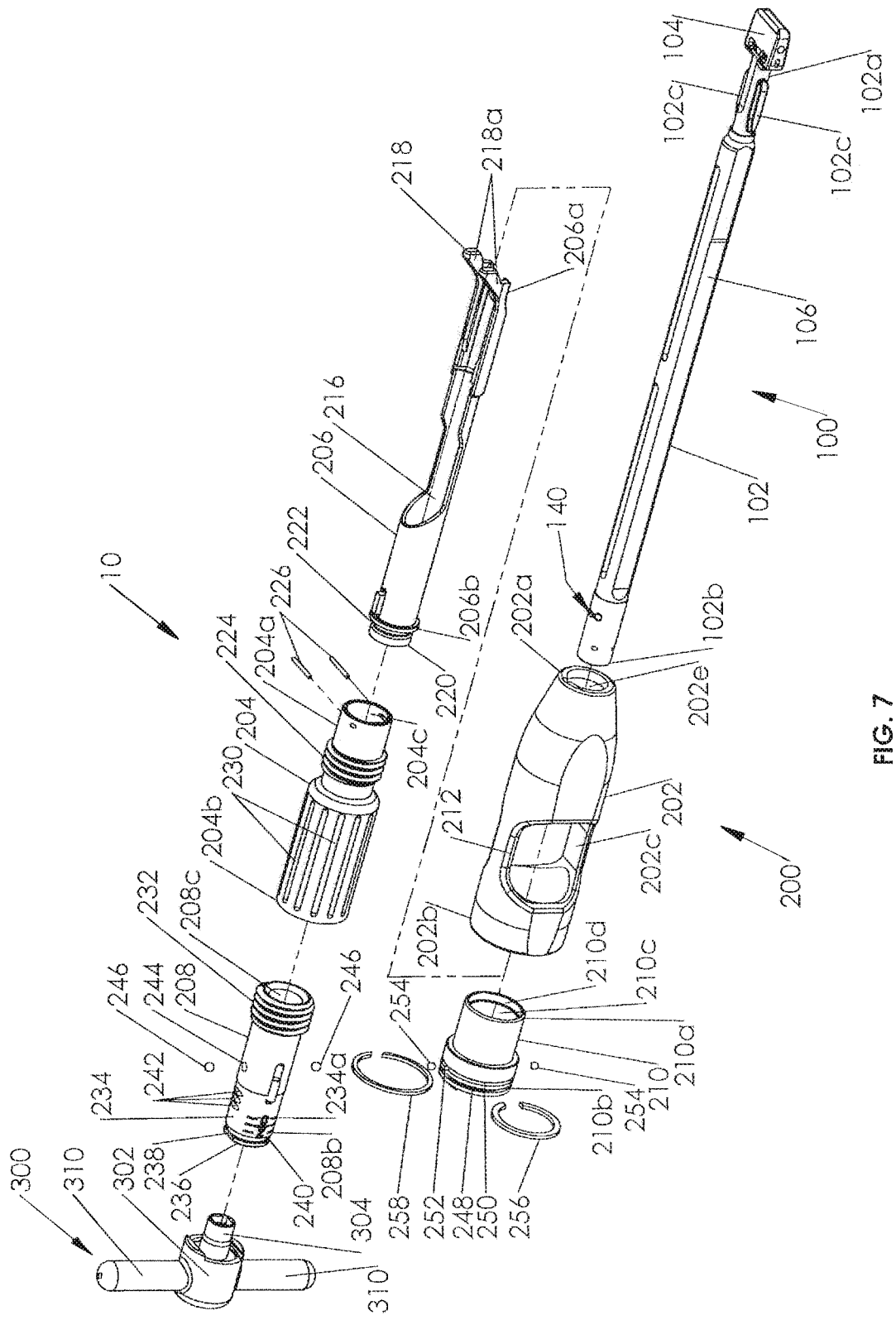
FIG. 7 is an exploded top perspective view of the disc preparation instrument of FIG. 1 showing components of the depth stop of the disc preparation instrument of FIG. 1.
Figure 8:
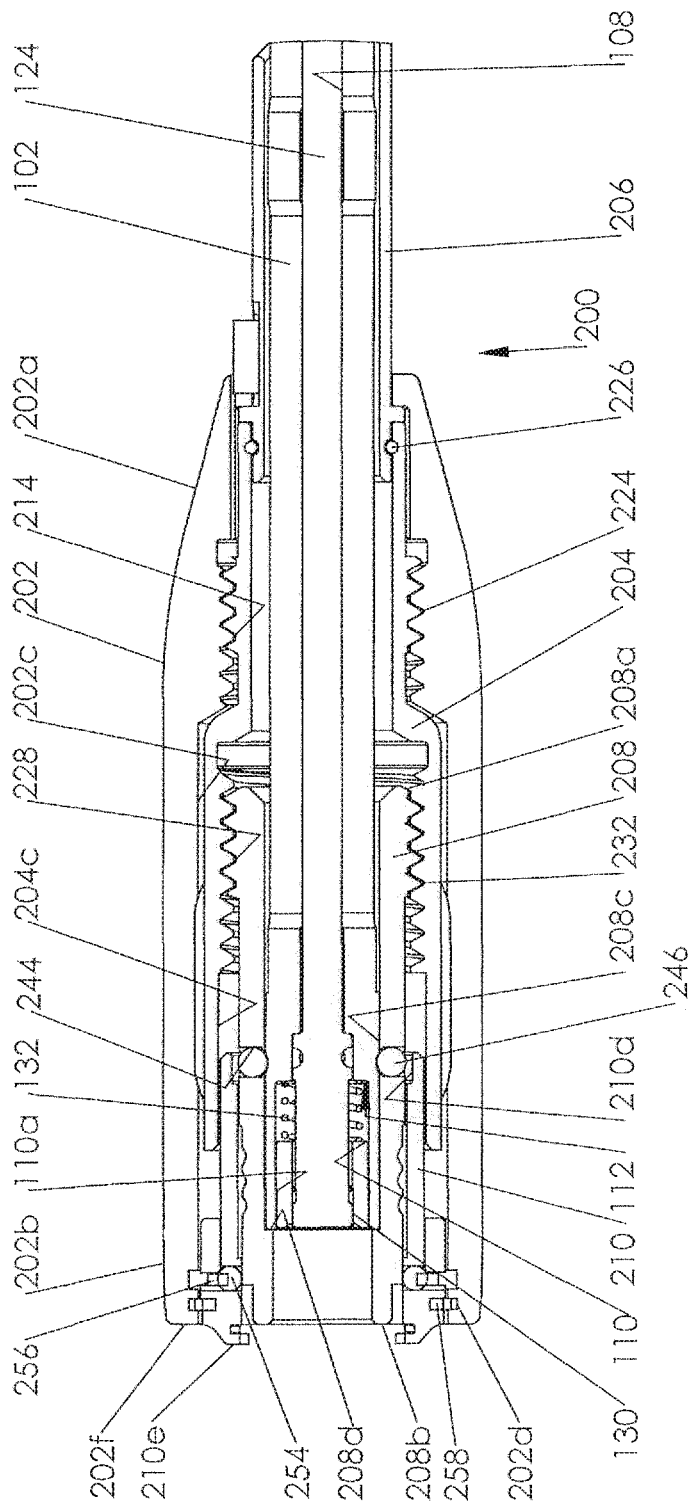
FIG. 8 is an enlarged longitudinal sectional view of the proximal portion of the disc preparation instrument of FIG. 2 before the T-handle is attached.

Turning now also to FIGS. 7 and 8, further details of the depth stop 200 are described. Depth stop 200 comprises a handle 202, an adjustment knob 204, an elongate sleeve 206, a center shaft 208 and a bushing 210. Handle 202 is generally cylindrical having a distal end 202a, a proximal end 202b, and an interior surface 202c within which adjustment knob 204 and center shaft 208 are disposed. Handle 202 includes a window 212 extending through an exterior surface to expose portions of adjustable knob 204. Interior surface 202c of handle 202 comprises internal threads 214 disposed adjacent the distal end 202a, as illustrated in FIG. 8. Threads 214 have a first predetermined pitch, such as 2 mm, with threads 214 being oriented in a first direction as a left-handed thread.

Elongate sleeve 206 is generally cylindrical having a distal end 206a and a proximal end 206b. Sleeve 206 has a partially open channel 216 extending generally centrally through sleeve 206 and through distal end 206a and proximal end 206b. Distal end 206a terminates in a stop 218 for measuring the depth of scoring element 122 from an exterior surface of a vertebra when the trial device 104 is inserted within an intervertebral disc space, as will be described. In a particular arrangement, stop 218 is defined by pair of opposed laterally spaced shoulders 218a having substantially flat interior surfaces. Each stop 218 may have an internally formed pocket 218b (see FIG. 12) for receipt of stabilizers 102c, as will be described. Channel 216 is of size and configuration to receive elongate stem 102 of modular scoring trial 100 such that flat surfaces 106 of scoring trial 100 are disposed closely adjacent flat surfaces of opposed shoulders 218a for proper orientation of trial device 104 relative to shoulders 218a. Proximal end 206b of sleeve 206 includes an attachment portion 220 including a circumferential groove 222.

Adjustment knob 204 is of generally cylindrical configuration having a distal end 204a and a proximal end 204b. Adjustment knob 204 includes external threads 224 adjacent distal end 204a that are threadably coupled with handle internal threads 214, threads 224 having the same first predetermined pitch and left-handed direction as handle internal threads 214 establishing a first threaded connection, as will be described. Proximal end 206b of sleeve 206 is coupled to distal end 204a of adjustment knob 204 by a set of pins 226 extending through sleeve 206 and into groove 222. Such coupling enables adjustment knob 204 and sleeve 206 to move axially jointly while allowing for rotational relative movement therebetween, movable stop 218 being affixed at the distal end 206a of sleeve 206. Interior surface 204c has adjacent the proximal end 204b of adjustment knob 204 internal threads 228, as illustrated in FIG. 8. Threads 228 have a second predetermined pitch, such as 2 mm, with threads 228 being right-handed threads and thereby oriented in a second direction, opposite the first direction of internal threads 214 of handle 202. In a particular arrangement, the second predetermined pitch of threads 228 is equal to that of the first predetermined pitch of threads 214. Adjustment knob 204 includes a plurality of axially extending circumferentially spaced splines 230 that are exposed through handle window 212, splines 230 facilitating the manual rotation of adjustment knob 204, as will be described.

Center shaft 208 is generally cylindrical having a distal end 208a, a proximal end 208b and an interior surface 208c. Distal end 208a comprises external threads 232, threads 232 having the same second predetermined pitch and right-handed direction as internal threads 228 of adjustment knob 204 for engagement in a second threaded connection, as will be described. An indicator device 234 at the proximal end 208b of center shaft 208 comprises a plurality of markings 234a, such as numerical indicia and gradations. Center shaft 208 further includes at its proximal end 208b a connection portion 236 for releasable attachment to actuator 300, as will be described. Connection portion 236 includes a pair of diametrically opposed substantially parallel flat surfaces 238 at proximal end 208b and a pair of diametrically opposed grooves 240 extending between flat surfaces 238 on either side of connection portion 236. Center shaft 208 in addition includes adjacent proximal end 208b a series of detent grooves 242 formed diametrically apart on the outer surface of center shaft 208, detent grooves 242 being spaced at predetermined axial intervals to correspond with increments of depth stop measurements as denoted by markings 234a of indicator device 234.

Center shaft 208 includes a pair of diametrically opposed openings 244 that are each formed to hold therein a ball bearing 246. Ball bearings 246 define a ball bearing lock for releasably locking center shaft 208 to scoring trial 100, as will be described. Each opening 244 extends radially through the wall of center shaft 208 and through interior surface 208c. Each ball bearing 246 has a diameter slightly greater than the wall thickness of center shaft 208 and is retained in a respective opening 244 such that ball bearings 246 may slightly move in the radial direction. In one position, each ball bearing 246 has a circumferential portion extending radially inwardly beyond interior surface 208c with a diametrically opposite circumferential portion being disposed within the wall of center shaft 208. In a second position, a circumferential portion of each ball bearing 246 extends radially outwardly beyond the exterior surface of center shaft 208 with the diametrically opposite circumferential portion being disposed within the wall of center shaft 208. Opposed openings 244 and ball bearings 246 are disposed on a line that is substantially perpendicular to opposing flat surfaces 238 at the distal end 208b of center shaft 208.

Bushing 210 is generally cylindrical having a distal end 210a, a proximal end 210b and an interior surface 210c. Interior surface 210c has a counterbore 210d at the distal end 210a of bushing 210. The inner diameter of counterbore 210d is greater than the inner diameter of inner surface 210c. Proximal end 210b of bushing 210 includes a pair of axially spaced circumferentially extending grooves 248 and 250. Groove 250 includes therewithin a pair of diametrically opposed openings 252 that are each formed to house therein a ball bearing 254. Each ball bearing 254 is resiliently retained in a respective opening 252 by a spring member, such as a C-clip 256 that is retentively supported within groove 250. C-clip 256 applies a radially inward bias force to ball bearings 254 in a manner that allows a circumferential portion of each ball bearing 254 to resiliently move inwardly and outwardly of interior surface 210c of bushing 210. As such, ball bearings 254 define a spring biased ball detent with grooves 242 on center shaft 208, as will be described A locking ring 258 is retained in groove 248 for connecting bushing 210 to interior surface 202c of handle 202 in the axial direction, as will be described.

Figure 9A:
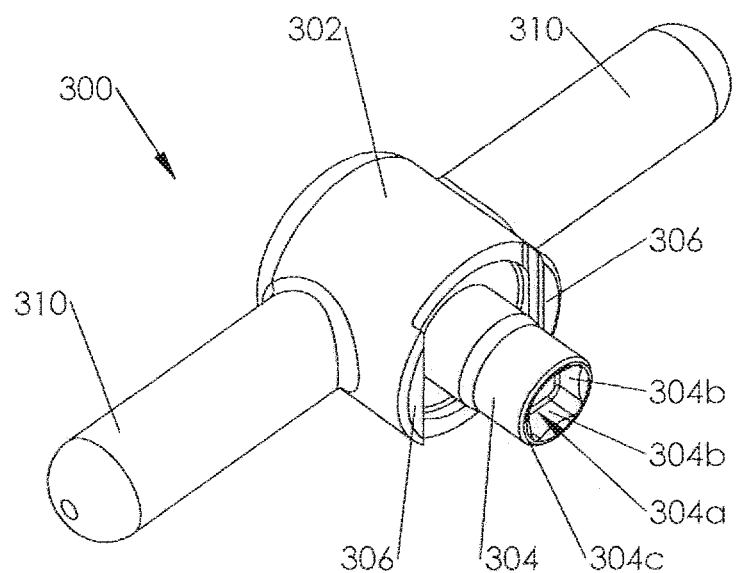
FIG. 9A is a perspective view of the T-handle of the disc preparation instrument of FIG. 1.
Figure 9B:
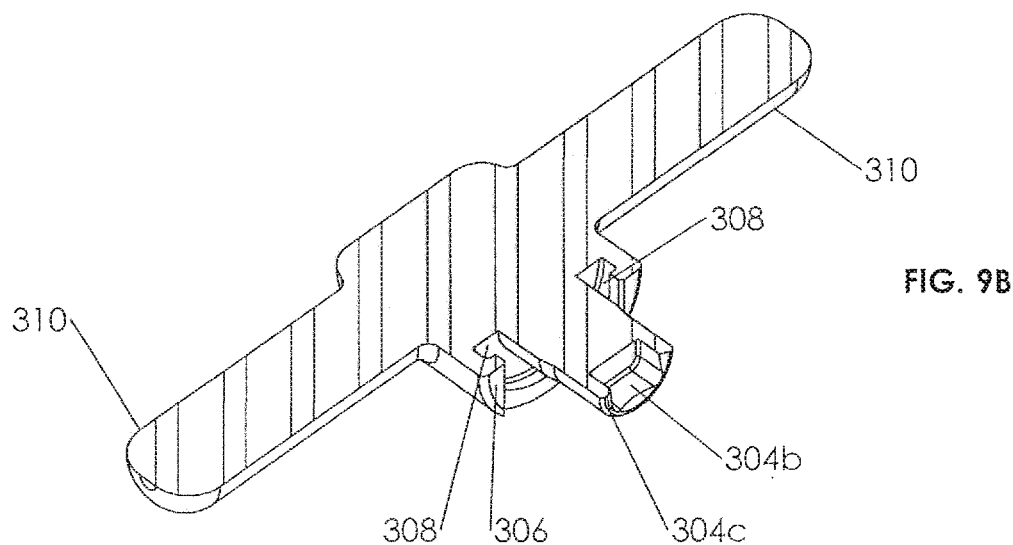
FIG. 9B is a cross sectional perspective view of the T-handle of FIG. 9A.

Turning now to FIGS. 9A and 9B, details of actuator 300 are described. Actuator 300 comprises a generally cylindrical central hub 302 including a drive portion 304 projecting axially therefrom. Drive portion 304 has a drive surface 304a configured to cooperatively mate with drive element 130 at the proximal end 124b of elongate shaft 124 of scoring trial 100. Drive surface 304a includes a non-circular configuration and, in a particular arrangement, comprises a square drive having four substantially flat mutually orthogonal engagement surfaces 304b that define a square socket of size and configuration to interface with the four substantially flat engagement surfaces 130a of drive element 130. Central hub 302 comprises a pair of diametrically opposed flanges 306 projecting axially distally therefrom, each flange 306 being defined by an undercut groove 308, as seen more particularly in FIG. 9B. Opposing flanges 306 are substantially parallel to each other with each flange 306 being oriented substantially parallel to one of flat surfaces 304b. Actuator 300 includes a pair of manually graspable extensions 310 projecting radially oppositely from central hub 302 and defining thereby a T-handle. Rotation of actuator 300 rotates elongate shaft 124 and thereby scoring element 122 of scoring trial 100. Extensions 310 are in alignment with each other and with flanges 306 to provide a visual indication of the orientation of scoring element 122 of scoring trial 100 in use. Central hub 302 includes at its distal end a contact surface 304c for contacting proximal end 134b of locking element 134 to apply an axial force thereto in the distal direction, as will be described.

The assembly of the components to form depth stop 200 is now described with continued reference to FIGS. 7 and 8. Sleeve 206 is rotatably attached to adjustment knob 204 by pins 226. This subassembly is introduced through handle 202 from proximal end 202b to 202a is shown by phantom line 260 in FIG. 7 with movable stop 218 being welded to sleeve 206 thereafter. External threads 224 of adjustment knob 204 are threadably engaged with internal threads 214 of handle 202 thereby forming the first threaded connection. Center shaft 208 containing ball bearings 246 is introduced into threaded knob 204 such that external threads 232 on center shaft 208 threadably engage internal threads 228 of adjustment knob 204 until proximal end 208b of center shaft 208 is approximately flush with proximal end 202f of handle 202, as depicted in FIG. 8, thereby establishing the second threaded connection. Bushing 210 with attached C-clip 256 residing in groove 250 and resiliently holding ball bearings 254 in openings 252 is attached to the interior surface 202c of handle 202 by snapping locking ring 258 into a groove 202d formed in interior surface 202c at the proximal end 202b of handle 202. In this condition as shown in FIG. 8, ball bearings 246 housed in the wall of center shaft 208 are in radial alignment with counterbore 210d of bushing 210, thereby allowing ball bearings 246 to radially float such that a circumferential portion of each ball bearing 246 extends within counterbore 210 while a diametrically opposing circumferential portion does not extend radially interiorly beyond interior surface 208c. In this condition, depth stop 200 is ready to receive scoring trial 100. Once in place, sleeve 206, handle 202 and bushing 210 are all suitably keyed with respect to each other in a manner to maintain relative radial alignment.

Figure 10:
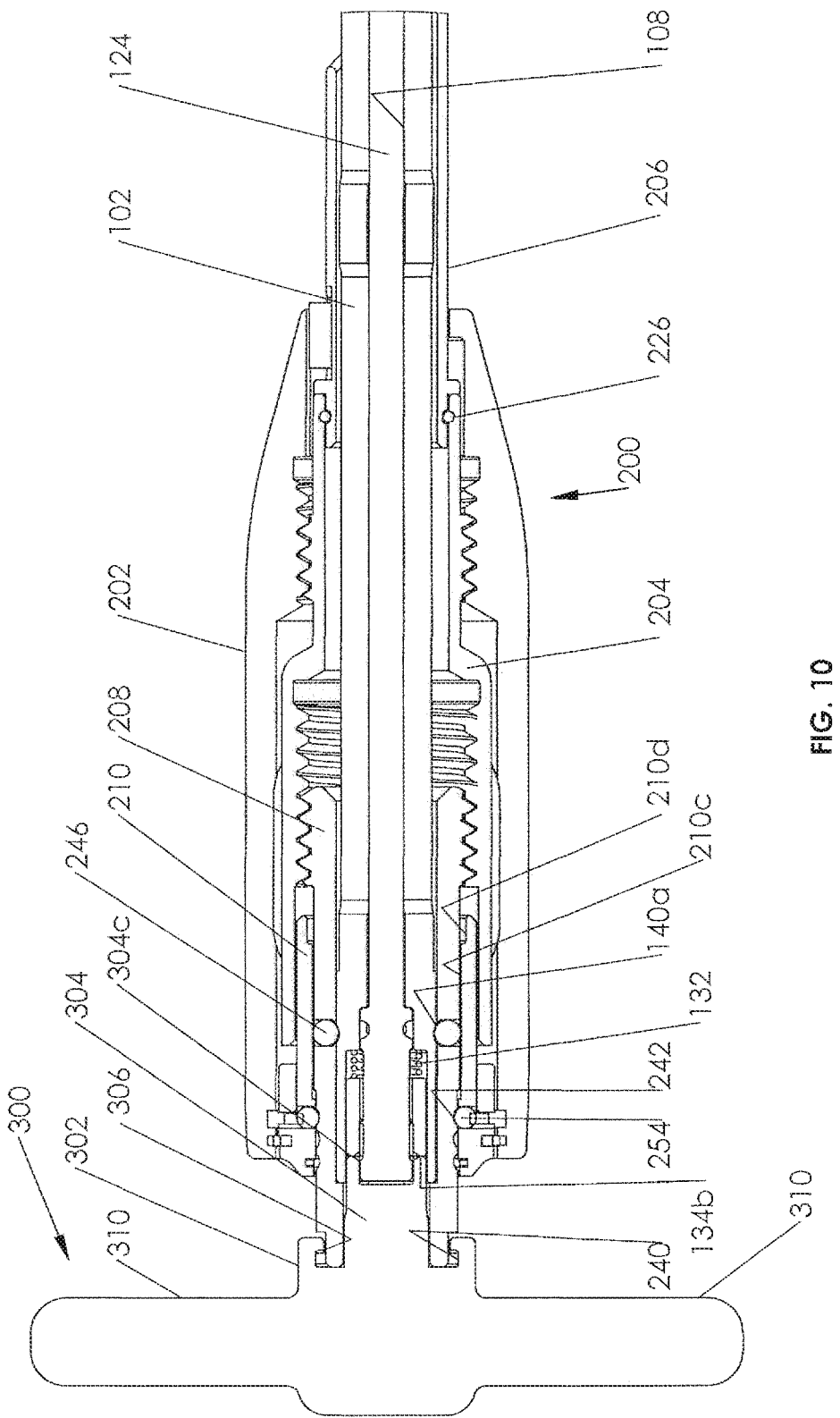
FIG. 10 is the sectional view of FIG. 8 with the T-handle attached.
Figure 11:
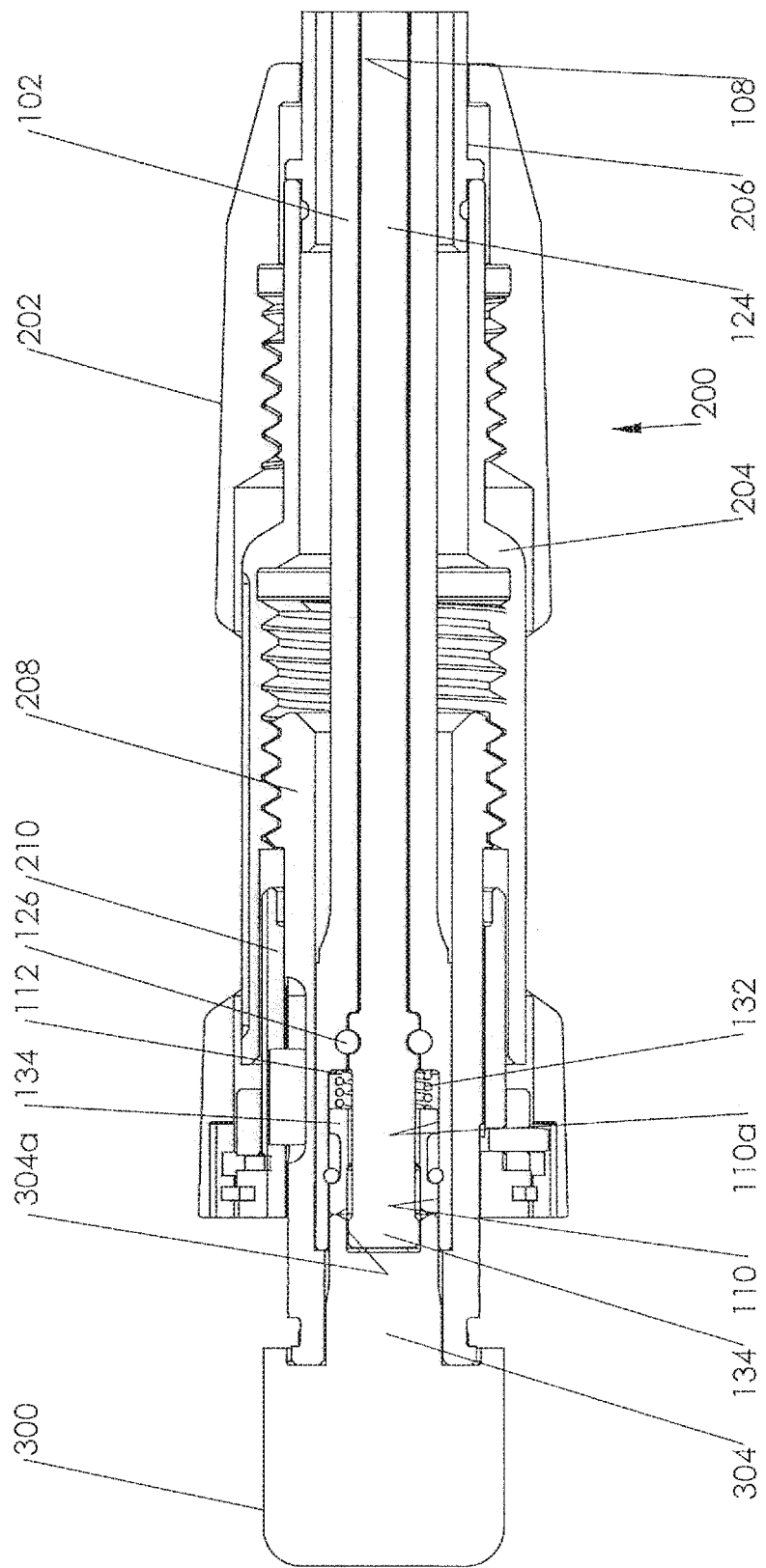
FIG. 11 is the proximal portion of the disc preparation instrument as seen along viewing lines XI-XI of FIG. 2.
Figure 12:
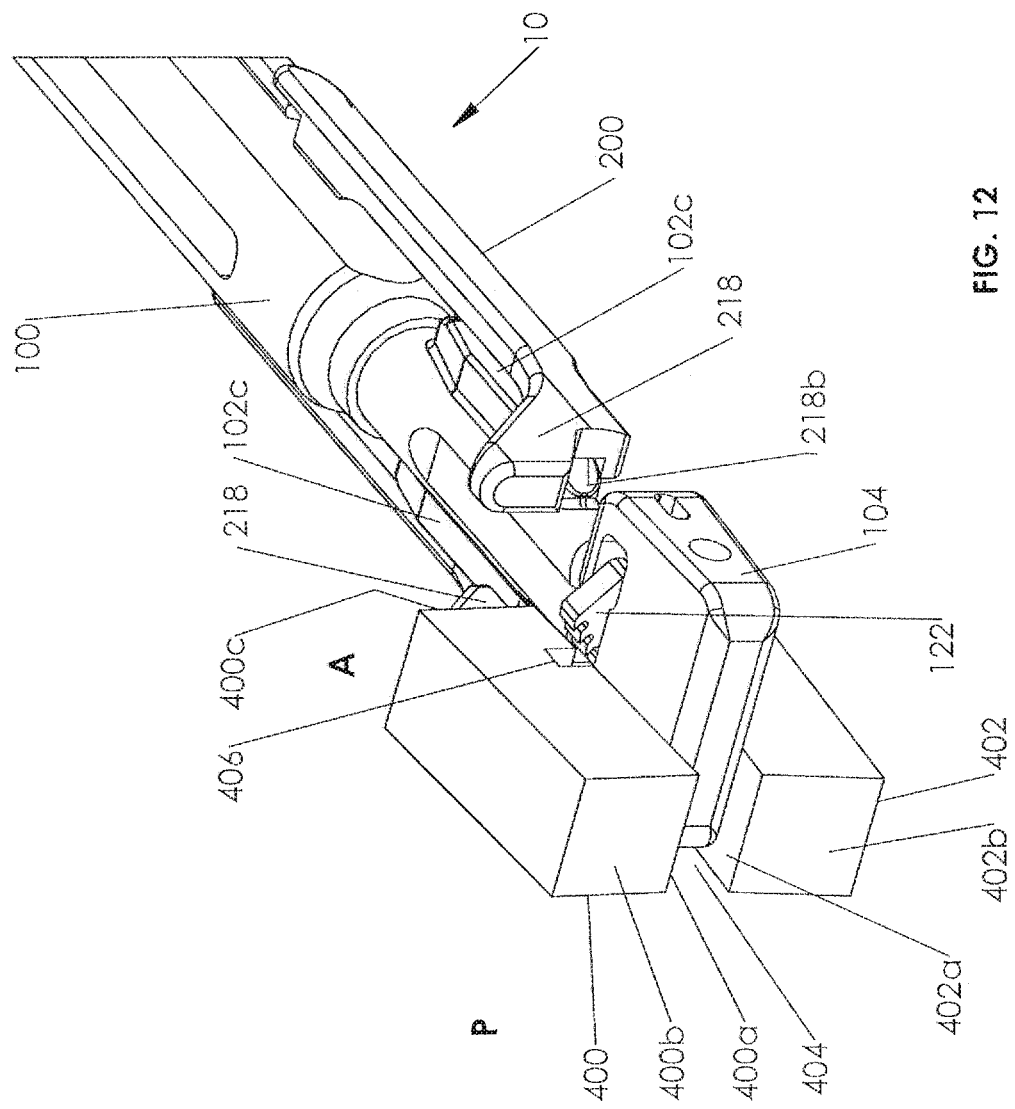
FIG. 12 is a perspective view showing the distal end of the disc preparation instrument with the trial device being disposed in an intradiscal space between two opposing vertebral bodies of a spine, the vertebral bodies being partially sectioned for clarity, the scoring element of the trial device being shown in a position forming a scored location in the endplates of the vertebral bodies.

With continued reference to FIGS. 7-8, and now also to FIGS. 10-11, the attachment of depth stop 200 and scoring trial 100 is described. Scoring trial 100 is introduced into depth stop 200 by initially radially introducing flat surfaces of shoulder 218a over flat surfaces 106 of elongate stem 102. Elongate stem 102 is then slid proximally axially within channel 216 and into opening 202e at the distal end 202a of handle 202 until proximal end 102b abuts counterbore 208d of center shaft 208, as shown in FIG. 8. During such proximal movement of stem 102, stabilizers 102c are received within pockets 218b of each stop 218, as shown in FIG. 12. Such interaction between stabilizers 102a and pockets 218b substantially prevents rotation of stem 102 relative to depth stop 200, thereby maintaining proper orientation of trial device 104 relative to shoulders 218a. At this point, attachment grooves 140a are in radial alignment with ball bearings 246 contained in center shaft 208. Adjustment knob 204 is then rotated clockwise through window 212 of handle 202 thereby activating the first and second connections, as described hereinabove. Such clockwise rotation causes adjustment knob 204 via the second threaded connection between threads 228 and 232 to move adjustment knob 204 axially in a distal direction relative to elongate stem 102. Additionally, such clockwise rotation of adjustment knob 204 via the first threaded connection between threads 214 and 224 causes handle 202 to also move axially distally relative to elongate stem 102. As a result, bushing 210 being axially attached to handle 202 also moves in a distal direction such that counterbore 210d is no longer radially aligned with ball bearings 246, as illustrated in FIG. 10. Rotation of adjustment knob 204 can continue until spring loaded detent ball bearings 254 engage the most distal detent grooves 242. The engagement of ball bearings 254 in respective detent grooves 242 creates a surmountable ball detent that provides tactile feedback and an audible click. The axial distal movement of handle 202 causes interior surface 210c of bushing 210 to engage ball bearings 246 and urge such ball bearings 246 into the locking grooves 140a of elongate stem 102, thereby establishing a rigid releasable locking connection between depth stop 200 and elongate stem 102 of scoring trial 100. Such locking connection is released by rotating adjustment knob 204 in a counterclockwise movement thereby proximally moving bushing 210 to the position of FIG. 8 whereby counterbore 210d is in radial alignment with ball bearings 246. Scoring trial 100 may then be readily removed distally from depth stop 200.

Referring again to FIGS. 9A, 9B and also to FIGS. 10-11, the releasable attachment of actuator 300 is described. Actuator 300 is releasably coupled to drive element 130 of elongate shaft 124 of scoring trial 100 in a manner to rotate scoring element 122 for scoring opposing vertebral endplates in preparation for receipt of anchor blades of an interbody fusion cage. To attach actuator 300 to drive element 130, actuator 300 is initially positioned with opposing flanges 306 oriented to be in alignment with opposing flat surfaces 238 on connection portion 236 of center shaft 208. In this orientation, flanges 306 may slide over flat surfaces 238 thereby allowing axially projecting drive portion 304 to extend into the interior of center shaft 208 at the proximal end 208b thereof. Contact surface 304c at the distal end of drive portion 304 contacts proximal end 134b of locking element 134 to apply an axial force thereto in the distal direction. Such axial force is sufficient to overcome the bias force applied in the proximal direction against locking element 134 by spring element 132. Under the application of the axial force provided by the distal movement of actuator 300, locking element 134 is urged in the distal direction releasing the integrated lock and exposing drive element 130, allowing attachment of square-drive surface 304a with square-drive element 130, as shown in FIG. 11. In this first position, actuator 300 may also be removed proximally from center shaft 208.

At this point, rotation of T-handle 300 in either the clockwise or counterclockwise directions to a second position will cause flanges 306 on actuator hub 302 to engage grooves 240 extending between flat surfaces 238 on either side of connection portion 236 of center shaft 208. Such engagement prevents removal of the T-handle until it is returned to the original first position or approximately 180 degrees opposite the original first position. Rotation of T-handle 300 in either direction rotates elongate shaft 124 and thereby scoring element 122 in a manner to score surfaces of opposing vertebral body endplates. Once the T-handle 300 begins to rotate it cannot be removed from center shaft 208 unless it is returned to its original location or 180 degrees opposite the original location. This arrangement alerts the surgeon to the position of the scoring element 122 within trial device 104 as the T-handle 300 may only be removed when the scoring element 122 is collapsed and the integrated lock 134 is enabled. Once the T-handle is returned to the original first position, T-handle 300 may be removed, and the surgeon may safely remove scoring trial 100 by pulling proximally outwardly on depth stop handle 200 without concern that scoring element 200 remains penetrated into the vertebral body.

Having described the disc preparation instrument 10, the function and operation of indicator device 234 is now described with particular reference to FIGS. 7-8 and FIG. 2. Indicator device 234 is operable with the axial distal movement of handle 202 relative to center shaft 208 to provide a visual indication of a plurality of selectable distances that stop 218 may move relative to trial device 104. As noted hereinabove, clockwise rotation of adjustment knob causes adjustment knob 204 via the second threaded connection between threads 228 and 232 to move adjustment knob 204 axially in a distal direction relative to elongate stem 102 which is axially affixed to trial device 104 at the distal tip of elongate stem 102. Additionally, such clockwise rotation of adjustment knob 204 via the first threaded connection between threads 214 and 224 causes handle 202 to also move axially distally relative to center shaft 208 which is releasably axially locked to elongate stem 102 by the ball bearings 246. Distal movement of adjustment knob 204 causes sleeve 206 and attached stop 218 to move distally relative stem 102 and thereby to a first location on trial device 104. It should be understood that counterclockwise rotation of adjustment knob 204 will cause adjustment knob 204 and handle 202 to move proximally relative to elongate stem 102 at the rates as described herein.

Such first location on the trial device 104 may be its proximal end 116, as shown in FIG. 2. Each distance, D, for example, that stop 218 is selectively spaced from proximal end 116 of trial device 104 is indicated by a different marking 234a that will be visually observable upon the axial distal movement of handle 202 which progressively exposes markings 234a at the proximal end of center shaft 208 relative to a reference element on depth stop 200. Such reference element in one approach is defined by end surface 210e at the proximal end of bushing 210. Alternatively, since bushing 210 is fixed axially relative to handle 202, the reference element may be defined by end surface 202f at the proximal end of handle 202. In a particular arrangement, markings 234a are two millimeters apart for ease of viewing but indicate one-millimeter increments of depth stop motion. This is accomplished via the two threaded connections (214/224 and 228/232) described above of substantially equal pitch but opposing directions. As such, when the adjustment knob 204 is rotated, relative axial translation between the handle 202 and center shaft 208 with markings 234a thereon occurs at twice the rate of axial translation between stop 218 and trial device 104. As a result, indicator device 234 provides an amplified indication of each of the selectively different distances, D between stop 218 and proximal end 116 of trial device 104. Such amplified indication allows a surgeon to more readily appreciate the location at which fusion cage may be placed in an intradiscal space, which is typically measured in millimeters and is relatively difficult to visually discern. It should be understood that while the threaded connections (214/224 and 228/232) are formed in opposing directions with each threaded connection having a pitch of 2 mm, similar differential rates of movement as described herein may be achieved with the threaded connections being in a common direction but of different pitches.

In this particular arrangement, indicator device 134 includes three indicia, denoted as "0", "1", and "2". The spacing in indicator device 234 between each of these markings is two millimeters, each of which represents a distance, D of 1 mm increment. The "0" marking may indicate a distance, D of approximately 2 mm, the "1" marking a distance, D of approximately 3 mm, and the "2" marking a distance, D of approximately 4 mm. As illustrated in FIG. 2, marking "2" is shown, indicating that stop 218 is measured at a distance, D of approximately 4 mm from trial device proximal end 116. Where the predetermined spacing, S between trial device proximal end 116 and the proximal surface of scoring element 122 is set, for example at 2 mm, the distance then between stop 218 and the proximal surface of scoring element 122 is determined to be 6 mm. As handle 202 translates distally relative to center shaft 208, spring biased detent balls 254 sequentially engage detent grooves 242 that are spaced apart at predetermined axial intervals corresponding to markings 234a on indicator device 234, provide tactile feedback and/or an audible click to the surgeon as each interval is reached. In the example shown in FIG. 2 where the marking "2" is shown detent balls 254 would be engaged in the most proximal set of grooves 242, and in the most distal set of grooves 242 when the indicator device 234 reads "0".

Having described the disc preparation instrument 10, a method for use in an interbody fusion procedure is described, with particular reference to FIG. 12. In one particular approach, disc preparation instrument 10 is used to prepare an intradiscal space for fusing together a superior vertebra 400 and an inferior vertebra 402 in the cervical region of the spine in a procedure known as a Smith-Robinson approach. It should be appreciated, however, that disc preparation instrument 10 may also be used in interbody fusion procedures in other regions of the spine. Superior vertebra 400 includes an inferior endplate 400a, a vertebral body 400b, and an exterior anterior surface 400c. Inferior vertebra 402 includes a superior endplate 402a, a vertebral body 402b and an exterior anterior surface 402c (not seen). Superior endplate 400a and inferior endplate 402a define an intradiscal space 404 therebetween. Endplates 400a, 402a consist primarily of relatively hard bony/cartilaginous material that is often difficult to penetrate for fixing fusion implants for interbody fusion purposes. In the cervical spine procedure, access to the spine is often provided by forming an incision through the anterior portion of the patient's neck to expose superior and inferior vertebrae 400,402. As such, exterior surfaces 400c, 402c of superior vertebra 400 and inferior vertebra 402, respectively, are anterior surfaces. A suitable discectomy is performed to provide an appropriate disc space 404 for receipt of a cage of the type described in the '051 Application or the '287 Application, each of which is incorporated by reference in its entirety herein. It should be understood that access may be provided in other approaches, such as posterior or lateral in lumbar/thoracic procedures, as well as in other spinal surgeries, such as corpectomies Disc preparation instrument 10 is used to suitably prepare opposing vertebral endplates 400a, 402a for receipt of a desired cage. Disc preparation instrument 10 is used to introduce trial device 104 at the distal tip thereof as described hereinabove into the disc space 404 using suitable imaging techniques, such as fluoroscopy. Such imaging includes a side view from the lateral perspective so that the depth of trial device 104 along the anterior-posterior (A/P) direction may be observed. Prior to introduction of the trial device 104 into the disc space the surgeon may set the indicator device 134 at a reading of "0", establishing a depth, D of approximately 2 mm. Should the surgeon determine that deeper penetration of a fusion cage is desired, the depth may be adjusted by rotating adjustment knob 204. Counterclockwise rotation causes adjustment knob 204 and sleeve 206 axially attached thereto to move proximally away from vertebral bodies 400, 402, allowing the fusion cage to be inserted deeper into the intradiscal space 404 until stop 218 at the distal end of sleeve 206 engages exterior surfaces 400c and 402c, as depicted in FIG. 12

Vertebral endplates 400a, 402a are then scored with disc preparation instrument 10. Scoring is effected by the rotation of T-handle 300 which rotates scoring element 122 from the first position to the second position, as illustrated in FIG. 12. Such rotation causes the abrasive edges of first portion 122a and second portion 122b of scoring element 122 to cut a slot 406 into endplates 400a, 402a. Complete penetration of slots 406 into the bony/cartilaginous endplates 400a, 402a may not be necessary as slots 406 at least provide a weakened, secured location to facilitate entrance of anchor plates on a fusion cage. T-handle 300 may be rotated clockwise or counterclockwise several times if necessary in order to suitably form scored location 406. After completion of the scoring procedure, disc preparation instrument 10 may be fully removed by manually pulling handle 202 in a proximal direction.

As can be appreciated, a surgeon may choose to use the scoring trial 100 with integrated scoring element 122 and integrated lock 134 for the sizing function, and once the scoring trial 100 has been deemed appropriate in size, attach the depth stop 200 without removing scoring trial 100 from the surgical site. Upon attachment, the surgeon can adjust the position of the depth stop 200 relative to trial device 100 by rotating depth stop adjustment knob 204. In performing this action, the depth stop handle 202 is automatically coupled to the scoring trial 100 via the ball bearing lock 246. Once the stop 218 is seated against the vertebral body, the surgeon can read the depth measurement from the graduations or markings located on the indicator device 234 at the proximal end of center shaft 208 that protrudes proximally from the proximal end of handle 202 and note this measurement for subsequent correlation with a cage inserter instrument, such as the inserter described in the '344 Application.

Figure 13:
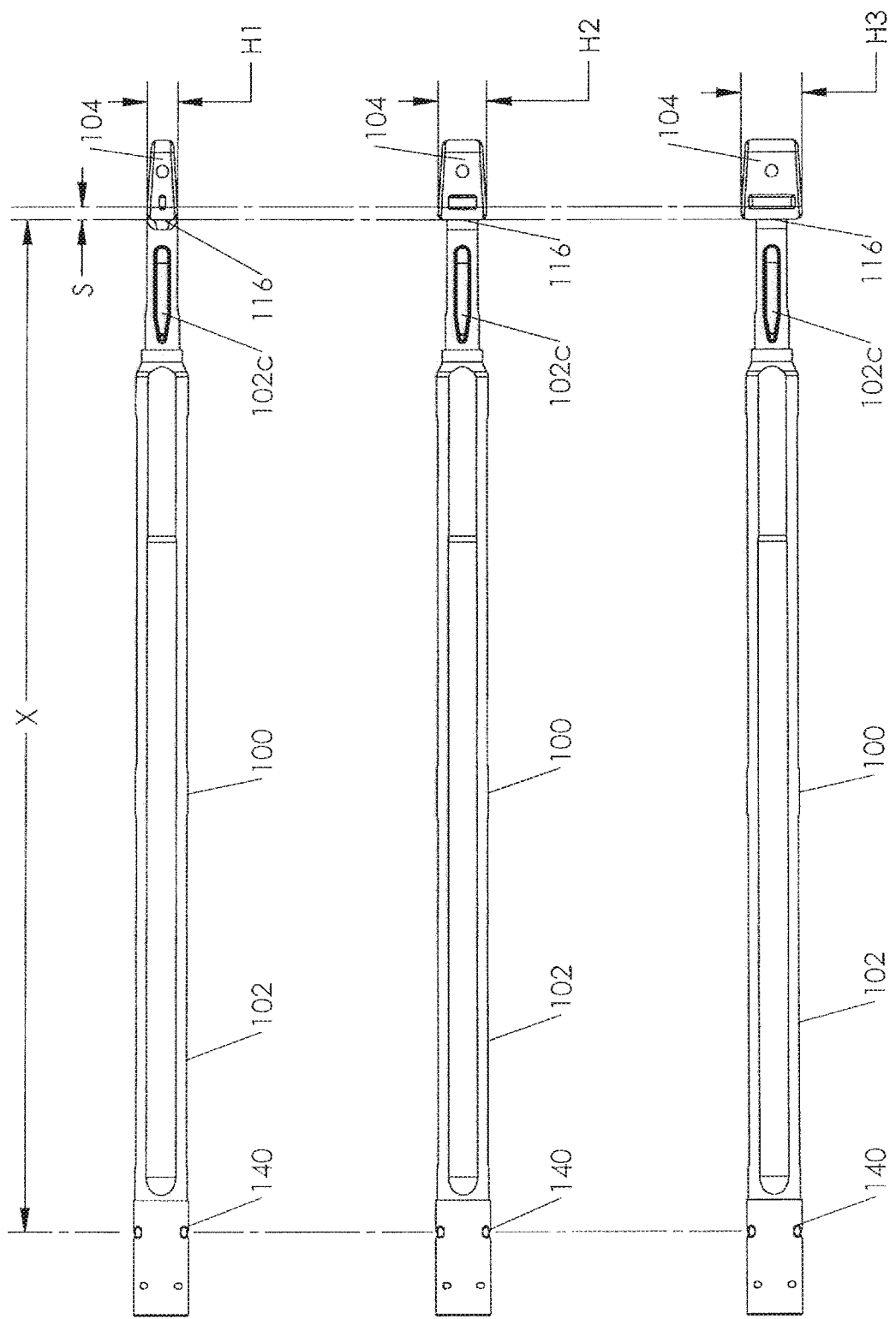
FIG. 13 is side elevational view of a plurality of modular scoring trials for use in a kit of parts in accordance with one aspect of the invention, each modular scoring trial having a trial device at the distal tip of differing heights.

In this regard, a plurality of modular scoring trials 100 as shown in FIG. 13, each having a trial device 104 of different heights, for example $H_1$, $H_2$ and $H_3$, may be provided in a kit. Each scoring trial 100 may be selectively releasably attached to a single depth stop 200. Each scoring trial 100 of the kit has an attachment location 140 on the stem 102 that is set at a fixed predetermined distance, X such as from attachment location 140 to proximal end 116 of a respective trial device 104. The fixed predetermined distance, X of each such modular scoring trial 100 is approximately the same. Further, the drive element 130 of the elongate shaft 124 of each modular trial 100 has substantially the same configuration and size.

As such, a variety of scoring trials 100 may be made available for use in assessing the size of the disc space 404 for selection of an appropriately sized fusion cage. A single T-handle 300 may be included in the kit together with a plurality of differently sized fusion cages to allow for selection based upon the assessment of disc space 406.

While the invention has been illustrated and described in detail in the drawings and foregoing description, it should be understood that such description is illustrative and not limiting. For example, an instrument for providing an amplified indication of a measured distance may be used in other surgeries where small dimensions are to be measured, typically in millimeters. Such surgeries, other than spinal surgery as described herein include, but are not limited to, maxillofacial surgeries and extremity surgeries, such as those involving the wrist. In such use, the instrument would comprise an elongate member having a distal end and a proximal end, the distal end of the elongate member including a first point of measurement and configured to be positioned within tissue of a patient. A movable stop having a surface defining a second point of measurement movable relative to the elongate member would be included, such stop being configured to contact a suitable surface of the patient. The movable stop would be movable to a plurality of selectable distances between the first point and the second point. An indicator device as described herein operable with the movement of the stop would be included to provide an amplified visual indication of each of the plurality of selectable distances It should therefore be understood that various changes, modifications and further applications may be made without departing from the spirit of the invention and the scope of the appended claims.

What is claimed is:

1. A depth stop for use in providing an amplified indication of a measured distance a surgical element is introduced into a disc space between two opposing vertebrae of a spine during spinal surgery, said depth stop comprising:
a handle having a distal end and a proximal end, said proximal end defining a reference element thereon, said handle comprising internal threads of a first pitch and first direction adjacent the distal end;
an adjustment knob having a distal end and a proximal end, said adjustment knob including external threads adjacent the distal end thereof and internal threads adjacent the proximal end thereof, said external threads being in the same first direction as and of approximately the same pitch as said internal threads of said handle and being threadably engaged therewith to define a first threaded connection, said internal threads of said adjustment knob having a second pitch and a second direction, said second direction being opposite said first direction, a sleeve attached to the distal end of said adjustment knob, said sleeve having a stop thereon movable with said adjustment knob, said stop being sized and configured to engage an exterior surface of one of said vertebrae; and
a center shaft having a distal end and a proximal end, said center shaft having external threads adjacent said distal end, said external threads being in the same second direction as said internal threads of said adjustment knob and of substantially the same pitch, said external threads of said center shaft being threadably engaged with said internal threads of said adjustment knob to define a second threaded connection, said center shaft including at said proximal end an indicator device comprising a plurality of markings,
wherein upon rotation of said adjustment knob on said center shaft in one direction, said adjustment knob and thereby said stop move distally relative to said center shaft at one rate and said handle and thereby said reference element thereon moves distally on said adjustment knob relative to said center shaft and thereby said indicator device markings at a second rate greater than said first rate.

2. The depth stop of claim 1, wherein the pitch of said first and said second threaded connections is substantially equal, thereby causing said second rate to be approximately twice said first rate.

3. The depth stop of claim 2, wherein said surgical element is a trial device sized and configured to be inserted into said disc space.

4. An instrument for providing an amplified indication of a measured distance between two points in surgery, said instrument comprising:
an elongate member having a distal end and a proximal end, the distal end of said elongate member including a first point of measurement and configured to be positioned within tissue of a patient,
a movable stop having a surface defining a second point of measurement movable relative to said elongate member, said stop being configured to contact an exterior surface of said patient, said movable stop being movable to a plurality of selectable distances between the said movable first point and said second point; and
an indicator device comprising a plurality of markings, said indicator device being operable with movement of said stop to provide an amplified visual indication of each of said plurality of selectable distances,
wherein said elongate member supports a reference element movable with movement of said movable stop relative to said indicator device to expose said markings of said indicator device at a rate greater than a rate of movement of said movable stop.

5. The instrument of claim 4, wherein said amplified indication is effected by first and second threaded connections between said elongate member and said movable stop.

6. The instrument of claim 5, wherein said first and second threaded connections are configured to be in opposite directions causing said movable stop and said reference element to move in the same direction relative to said indicator device.

7. The instrument of claim 6, wherein a pitch of said first and second threaded connections is substantially equal, thereby causing said reference element to move at a rate approximately twice the rate movement of said movable stop.

8. The instrument of claim 7, wherein said instrument is an instrument for use in fusing together a superior vertebra and an inferior vertebra, the superior vertebra including an inferior endplate and a vertebral body, the inferior vertebra including a superior endplate and a vertebral body, the superior and inferior endplates defining a disc space therebetween, said elongate member having at its distal end an element sized and configured for insertion into said disc space, said first point of measurement being located on said element.

\* \* \* \* \*